United States Patent
Zhang et al.

(10) Patent No.: US 11,850,066 B2
(45) Date of Patent: Dec. 26, 2023

(54) SYSTEM FOR MEASURING AND MONITORING BLOOD PRESSURE

(71) Applicant: THE GENERAL HOSPITAL CORPORATION, Boston, MA (US)

(72) Inventors: Quan Zhang, Winchster, MA (US); Yuanting Zhang, Hong Kong (CN)

(73) Assignee: The General Hospital Corporation, Boston, MA (US)

( * ) Notice: Subject to any disclaimer, the term of this patent is extended or adjusted under 35 U.S.C. 154(b) by 268 days.

(21) Appl. No.: 15/032,933

(22) PCT Filed: Oct. 31, 2014

(86) PCT No.: PCT/US2014/063374
§ 371 (c)(1),
(2) Date: Apr. 28, 2016

(87) PCT Pub. No.: WO2015/066445
PCT Pub. Date: May 7, 2015

(65) Prior Publication Data
US 2016/0262695 A1    Sep. 15, 2016

Related U.S. Application Data

(60) Provisional application No. 61/898,199, filed on Oct. 31, 2013.

(51) Int. Cl.
*A61B 5/00* (2006.01)
*A61B 5/022* (2006.01)
(Continued)

(52) U.S. Cl.
CPC .......... *A61B 5/6803* (2013.01); *A61B 5/0022* (2013.01); *A61B 5/022* (2013.01);
(Continued)

(58) Field of Classification Search
CPC ............ A61B 5/021; A61B 2562/0247; A61B 2562/046; A61B 5/6814; A61B 2562/164;
(Continued)

(56) References Cited

U.S. PATENT DOCUMENTS 4,269,193 A * 5/1981 Eckerle .............. A61B 5/02116
600/485
5,065,765 A * 11/1991 Eckerle .................. A61B 5/021
128/901

(Continued)

FOREIGN PATENT DOCUMENTS

CN         2824836 Y    10/2006

OTHER PUBLICATIONS

International Search Report and Written Opinion dated Apr. 8, 2015 in connection with PCT/US2014/063374.

*Primary Examiner* — Carrie R Dorna
*Assistant Examiner* — Karen E Toth
(74) *Attorney, Agent, or Firm* — Quarles & Brady LLP

(57) ABSTRACT

A system and method for measuring and monitoring blood pressure is provided. The system includes a wearable device and a tonometry device coupled to the wearable device. The Tonometry device is configured to compress a superficial temporal artery (STA] of a user. A sensor pad is attached to the wearable device adjacent the tonometry device. A blood pressure sensor is integrated within the sensor pad for continuous, unobtrusive blood pressure monitoring.

27 Claims, 9 Drawing Sheets

(51) Int. Cl.
  *A61B 5/33* (2021.01)
  *A61B 5/021* (2006.01)
  *A61B 5/026* (2006.01)
  *A61B 5/0245* (2006.01)
  *A61B 5/024* (2006.01)
  *A61B 5/0205* (2006.01)

(52) U.S. Cl.
  CPC .......... *A61B 5/026* (2013.01); *A61B 5/02125* (2013.01); *A61B 5/33* (2021.01); *A61B 5/7278* (2013.01); *A61B 5/7282* (2013.01); *A61B 5/742* (2013.01); *A61B 5/0002* (2013.01); *A61B 5/0245* (2013.01); *A61B 5/02055* (2013.01); *A61B 5/0261* (2013.01); *A61B 5/02108* (2013.01); *A61B 5/02416* (2013.01); *A61B 2560/0223* (2013.01); *A61B 2562/0247* (2013.01); *A61B 2562/04* (2013.01); *A61B 2562/046* (2013.01); *A61B 2562/12* (2013.01); *A61B 2562/164* (2013.01)

(58) Field of Classification Search
  CPC .... A61B 5/6803; A61B 5/6843; A61B 5/0053
  See application file for complete search history.

(56) References Cited

U.S. PATENT DOCUMENTS

| | | | | |
|---|---|---|---|---|
| 5,158,091 | A * | 10/1992 | Butterfield | A61B 5/021 600/485 |
| 6,251,080 | B1 * | 6/2001 | Henkin | A61B 5/02233 600/490 |
| 6,290,650 | B1 * | 9/2001 | Butterfield | A61B 5/021 600/485 |
| 6,443,906 | B1 | 9/2002 | Ting et al. | |
| 6,533,729 | B1 * | 3/2003 | Khair | A61B 5/021 600/480 |
| 7,479,111 | B2 | 1/2009 | Zhang et al. | |
| 2002/0062086 | A1 * | 5/2002 | Miele | A61B 5/02028 600/483 |
| 2007/0219447 | A1 * | 9/2007 | Kanai | A61B 8/0858 600/450 |
| 2008/0064968 | A1 * | 3/2008 | Martin | A61B 5/7282 600/493 |
| 2008/0194917 | A1 * | 8/2008 | Muehlsteff | A61B 5/00 600/300 |
| 2010/0011036 | A1 | 5/2010 | Chaum | |
| 2010/0110368 | A1 * | 5/2010 | Chaum | G02B 27/017 351/158 |
| 2010/0298650 | A1 * | 11/2010 | Moon | A61B 5/044 600/301 |
| 2010/0298665 | A1 | 11/2010 | Uenishi et al. | |
| 2010/0312115 | A1 * | 12/2010 | Dentinger | A61B 5/02116 600/450 |
| 2011/0257540 | A1 * | 10/2011 | Sawanoi | G01G 23/16 600/494 |
| 2011/0288419 | A1 * | 11/2011 | Baruch | A61B 5/02125 600/485 |
| 2012/0232387 | A1 * | 9/2012 | Miyachi | A61B 5/02007 600/438 |
| 2013/0171599 | A1 | 7/2013 | Bleich et al. | |

* cited by examiner

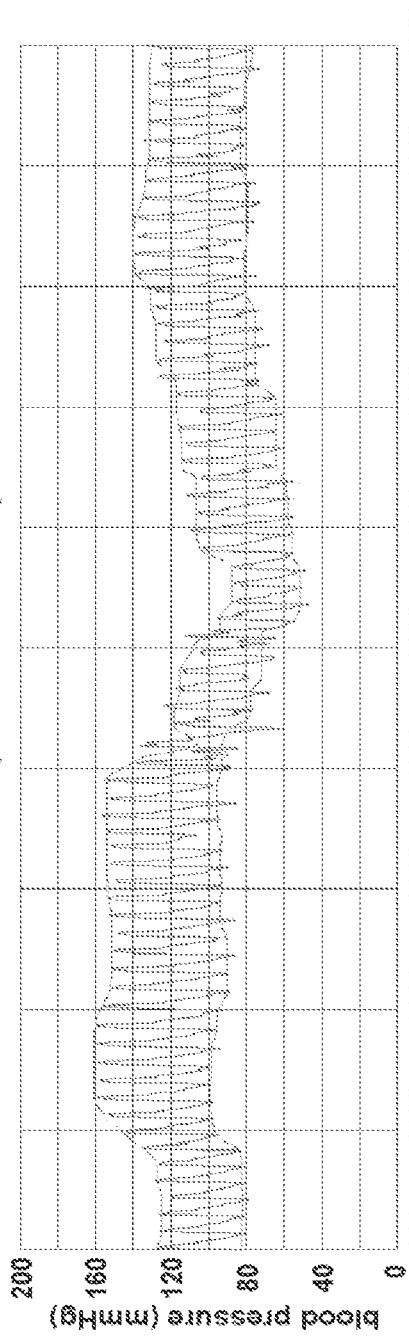
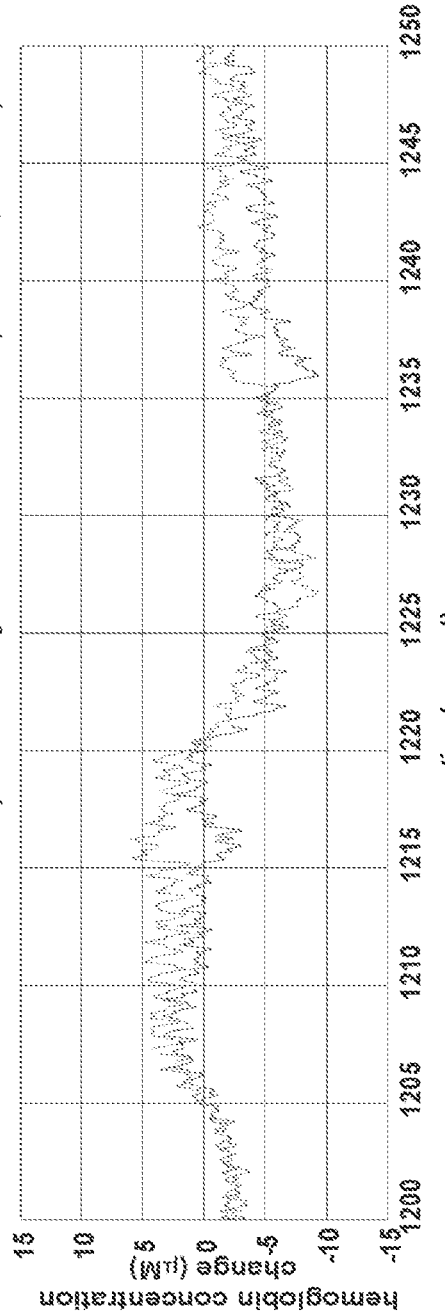
FIG. 7A
FIG. 7B

SYSTEM FOR MEASURING AND MONITORING BLOOD PRESSURE

CROSS-REFERENCE TO RELATED APPLICATIONS

This application is a 371 application of PCT/US2014/063374 filed Oct. 31, 2014 which claims the benefit of U.S. Provisional Application Ser. No. 61/898,199, filed Oct. 31, 2013, all of which are incorporated herein by reference for all purposes.

STATEMENT OF FEDERALLY SPONSORED RESEARCH OR DEVELOPMENT

The invention was made with goverment support under EB022271 awarded by the National Institutes of Health. The government has certain rights in the invention.

BACKGROUND

Cardiovascular disease (CVD) is the leading cause of death and lower life expectancy worldwide. Hypertension is one of the most significant risk factors for CVDs, such as heart attack and stroke, in the United States and India. Timely diagnosis and management of hypertension are both of critical need, as an increase in the prevalence of obesity has correlated with an increase in hypertension in both young people and older adults. Heart disease has been found to be the cause of one in every four deaths, and heart attack and stroke are the first and fourth leading causes of death in the United States, respectively. Additionally, over $450 billion is spent annually to cover the health care needs of over 2 million patients who suffer heart attack and stroke. Central to any therapy for these patients is an accurate measurement of blood pressure.

Blood pressure (BP) measurements are also needed when anesthesia has been administered, and for patients receiving emergency and critical care. In these cases, it would be desirable to have noninvasive, continuous blood pressure measurements to provide immediate feedback indicative of the state of the patient. Continuous blood pressure measurements would also be beneficial when performing studies of cardiac function, arterial elasticity, autonomic function, cerebral autoregulation, physiological measurements in aerospace research, and the like.

The current cuff-based arterial blood pressure (ABP) measurement technique (i.e., the Kortkoff method) is over 100 years old and is utilized in both private homes and healthcare establishments such as clinics, operation theatres, hospital wards, and accident and emergency departments. ABP measurement provides for an initial clinical assessment for hypertension or hypotension, and serves as an important parameter in a wide range of physiological research. Most conventional ABP measurement technologies involve the use of cuff and the inflation/deflation procedure. Although relatively accurate, existing ABP measurement technologies are slow and less compatible with electronic health record (EHR) systems than alternative methods.

In addition, the Korotkoff measurement technique presents several other disadvantages. For example, the method is only indicative of the BP status of a small portion of the entire 24-hour blood pressure pattern, and often the time of measurement is not specified; therefore, identification of hypertension and categorization of the severity levels are highly ambiguous due to significant BP variability throughout the day. Further, when using the cuff-based method, BP can be affected by environmental error such as the "white-coat" effect resulting in erroneous BP measurements. BP measurements acquired using the Korotkoff method can also be affected by defects in cuff instrumentation, and improper technique and measurement procedures by inadequately trained personnel can lead to errors in measurement. Finally, the Korotkoff method is not efficient in identifying cases like nighttime hypertension when high or low values may occur only at certain times during the 24-hour cycle.

Without the information pertaining to the circadian BP patterning and the sleep BP level, it is estimated that identification of high-risk subjects using Korotkoff method BP measurements lead to potential misclassification of up to 50% of all evaluated individuals. Additional existing methods for blood pressure measurement include the use of an arterial line, oscillometric measurement, peñás, tonometry, and pulse transit time. It has been found, however, that each of these methods demonstrate different limitations as well. Oscillometric measurements can be erroneous based on incorrect cuff size, arterial lines present a health risk to the patient and require trained personnel for placement, peñás is expensive and can be affected by factors such as cold extremities, tonometry is expensive, and pulse transit time has yet to be fully developed to correlate to blood pressure. In addition, these methods are difficult to integrate into EHRs and are subject to human error.

Thus, an unobtrusive and EHR compatible technique for blood pressure measurement and continuous monitoring that combines the latest wearable computing and information technologies would be desirable, and may present particular benefits in underserved populations.

SUMMARY OF THE INVENTION

The present invention overcomes the aforementioned drawbacks by providing systems and methods for measuring and monitoring a patient's blood pressure non-invasively using a cuffless device which provides for continuous, unobtrusive monitoring and measurement of a user's arterial blood pressure (ABP). A wearable device is configured to compress the user's superficial temporal artery (STA) using a tonometer, and a blood pressure sensor provides real-time ABP measurements during daily activities.

In accordance with one aspect of the invention, a blood pressure measurement and monitoring device is disclosed. The system includes a wearable device and a tonometry device coupled to the wearable device. The tonometry device is configured to compress a superficial temporal artery (STA) of a user. A sensor pad is attached to the wearable device adjacent the tonometry device. A blood pressure sensor is integrated within the sensor pad for continuous, unobtrusive blood pressure monitoring.

In accordance with another aspect of the invention, a method for monitoring blood pressure is disclosed. The method includes compressing the superficial temporal artery (STA) using a tonometer and sensing cardiac pulses of the STA with at least one blood pressure sensor. The sensed cardiac pulses are received from the blood pressure sensor and provided into an algorithm stored on an electronic control unit. An arterial blood pressure measurement from the algorithm is displayed on a user interface.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The present invention will hereafter be described with reference to the accompanying drawings, wherein like reference numerals denote like elements.

FIG. 7A is a graphical representation of measured blood pressure over time acquired using ambulatory STA tonometry during micturition.

FIG. 7B is a graphical representation of measured oxygenated hemoglobin and reduced hemoglobin concentrations acquired during micturition.

DETAILED DESCRIPTION OF THE INVENTION

Figure 1:
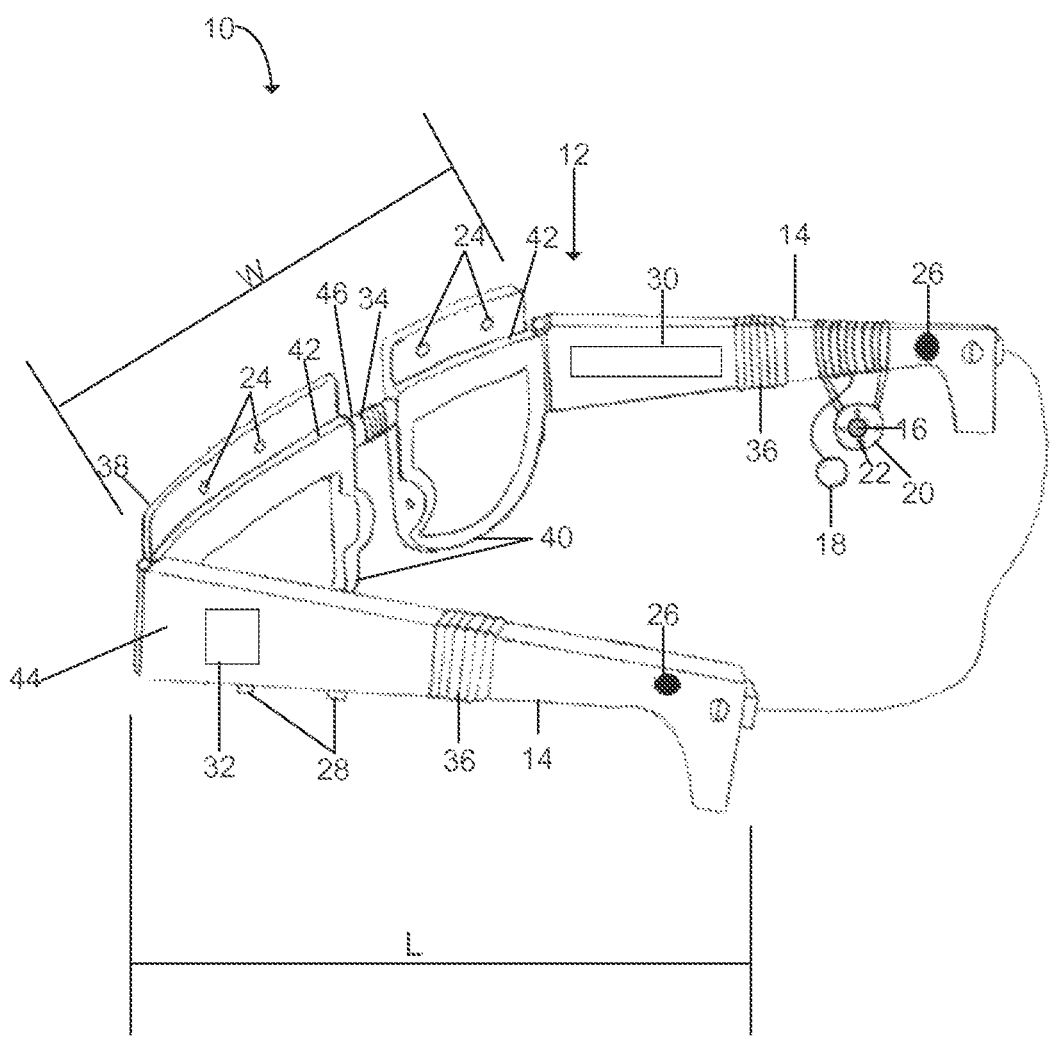
FIG. 1 is a perspective view of a blood pressure management system according to one embodiment of the present disclosure.

Referring particularly now to FIG. 1, a blood pressure management system 10 is shown. The blood pressure management system 10 may include a wearable device 12, for example a pair of glasses, a headband, a hat, headphones, and the like. In one embodiment, the wearable device 12 is a pair of glasses having a frame 38, comprised of two lenses 40 connected by a bridge 46, and a support 14 (i.e., a temple) coupled to and extending from each lens 40. The support 14 may have coupled thereto a blood pressure sensor 16, such as an ABP sensor. By integrating the blood pressure sensor 16 with the wearable device 12, the blood pressure management system 10 may be unobtrusive due to the wearable device 12 being small in size, light weight, and often worn daily by many people. Thus, the unobtrusive blood pressure management system 10 allows for a user to proactively monitor blood pressure without interrupting daily activities. Additionally, the blood pressure management system 10 may help the user to recognize potential cardiovascular disease at an earlier stage and before side effects become irreversible.

To provide a blood pressure measurement system 10 suitable for different individuals, the frame 38 and supports 14 can be provided in multiple sizes. As such, the width W, and the support length L, can be adjustable, to meet individual requirements. The width W of the frame 38 may be adjusted with a width adjuster 34 integrated within the bridge 46. Similarly, the length L may be adjusted with length adjusters 36 integrated within the supports 14 of the frame 38. In one non-limiting example, prescription lenses may be incorporated into the lenses 40 of the frame 38. Advantageously, the weight of the wearable device 12 does not impede the user's comfort. It is also possible for the blood pressure monitoring components to be provided in a compact structure such that they can be clipped onto an individual's glasses or sunglasses.

ABP can be measured using STA tonometry. When measuring blood pressuring using STA tonometry, a tonometer 18 may be placed over the STA of the user. The tonometer 18 compresses the STA until the vessel is flattened against the bony support below the STA, but the vessel is not fully occluded. The blood pressure sensor 16 on the skin surface can then measure ABP via contact pressure.

With continued reference to FIG. 1, the blood pressure sensor 16 may be integrated within an adjustable sensor pad 20 connected to the support 14 to allow for blood pressure measurement. The blood pressure sensor 16 may be configured for continuous measurement of the user's ABP, allowing for detection of heart disease and stroke based on the transient symptoms that may not be recognized using current methods. In one non-limiting example, the sensor pad 20 may be adjustable, such that the pressure, location, and pressing angle of the blood pressure sensor 16 allow for acquisition of near maximum pulsation. In one embodiment, a spring (not shown) provides a spring loaded sensor pad structure, which allows for adjustable pressure level and stable external pressure on the STA. Additionally, or alternatively, when using the blood pressure management system 10, the user can identify the STA, position the sensor 16, apply the sensor pad 20, and fine-tune the position of the sensor 16 and the sensor pad 20 to enable sufficient STA coverage. In some embodiments, screws (not shown) may be implemented to allow for the user to change the pressure and angle of the adjustable sensor pad 20.

In a further embodiment, the system 10 also includes a wrist blood pressure meter (not shown) to assist with calibration of the blood pressure sensor 16. The blood pressure sensor 16 measures relative blood pressure changes, and thus it may be desirable to have the wrist blood pressure meter to provide additional blood pressure measurements. The blood pressure sensor 16 output is calibrated using the wrist blood pressure meter, and the blood pressure may be calculated using an algorithm. In some embodiments, the sensor is calibrated using hydrostatic calibration instead of the wrist blood pressure meter. It is also possible to incorporate a long term ambulatory recorder (not shown) within the system to enable recording of the patient's blood pressure during daily activities.

The blood pressure management system 10 may further include one or more optical hemodynamic sensors 22 that are integrated within the adjustable sensor pad 20. The optical hemodynamic sensors 22 may be capable of recording changes in tissue hemodynamic signals, which allow for measurement of tissue hemodynamic signals and the calculation of changes in tissue oxygenated hemoglobin and reduced hemoglobin concentrations. In one non-limiting example, the hemodynamic sensors 22 may be integrated within the support 14 or any suitable location on the frame 38 that is not obtrusive to the user. It is also possible to incorporate one or more pulse transit time (PTT) or pulse wave velocity (PWV) sensors (not shown). The PTT and/or PWV sensor can be used to measure the time or speed of a cardiac pulse propagation along a blood vessel or set of blood vessels. Additionally, one or more auxiliary sensors 24 (e.g., temperature sensors), may be attached to an upper edge 42 of each lens 40 to assist with ABP measurements. The auxiliary sensors 24 can also be attached to the wearable device 12 in any feasible location that is not obtrusive to the user. Further, a battery 32 may be installed within the frame 38 or one of the supports 14 to power the various sensors. The battery 32 may be a lithium-ion battery, for example, integrated on an outer surface 44 of the support 14.

Figure 2:
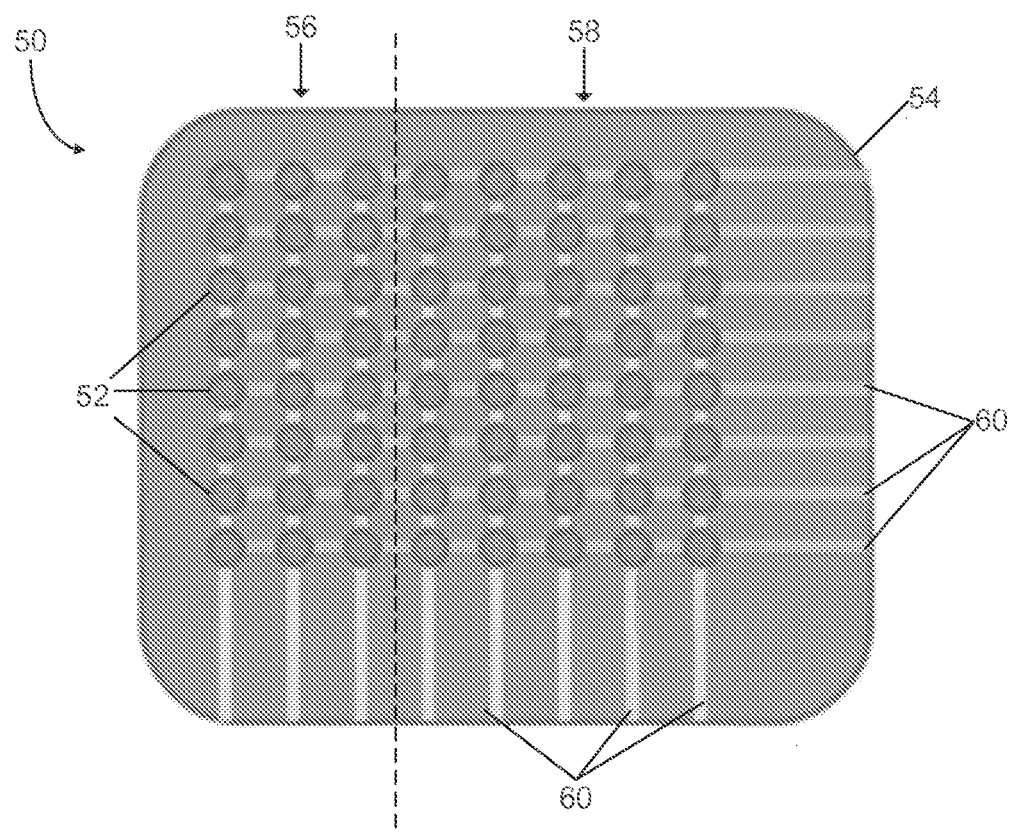
FIG. 2 is a diagram of an example sensor array to be implemented into the blood pressure management system of FIG. 1.

In some embodiments, a sensor array 50, as shown in FIG. 2, may replace the blood pressure sensor 16 to allow for increased accuracy when measuring blood pressure via STA tonometry. The sensor array 50 includes a plurality of sensors 52 integrated into a substrate 54, such as a flexible Parylene substrate. By incorporating the plurality of sensors 52 in the substrate 54, the sensor array 50 demonstrates biocompatibility. More specifically, parylene has a high toughness and has the ability to be used as a substrate for electrical contacts. The substrate 54 is also flexible and allows the sensor array 50 to conform to the nonplanar geometries involved when placed over the STA.

With continued reference to FIG. 2, the sensor array 50 may be a two dimensional array for measuring waveforms of blood pressure signals using tonometery. In one non-limiting example, the sensor array 50 may have dimensions of about 1 centimeter by about 2 centimeters, with approximately a 1 millimeter resolution. Additionally, the sensor array 50 may include a soft, flexible, and conformal packaging, have sufficient bandwidth for continuous measurement, and a dynamic range and resolution specified in the IEEE 1708™ "Standard for Wearable Cuffless Blood Pressure Measuring Devices".

Figure 3:
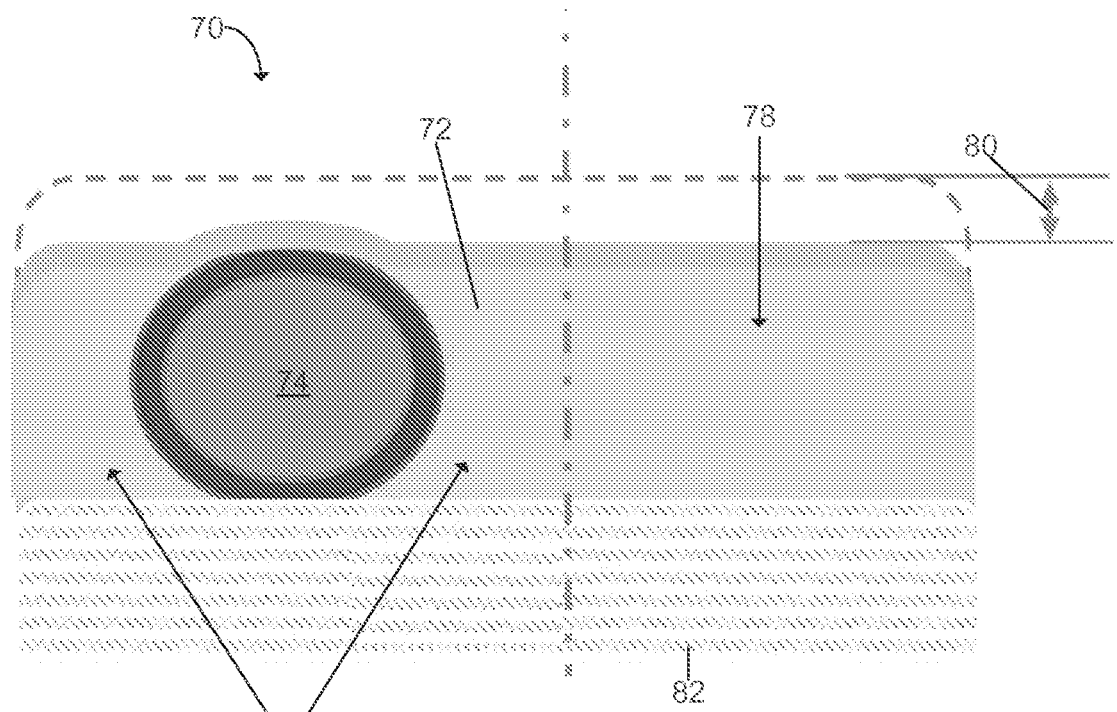
FIG. 3 is an STA tonometry model for an embodiment of the sensor array of FIG. 2.

Turning now to FIG. 3, an STA tonometry model 70 is shown. Tissue 72 near an STA 74 is divided into a testing region 76 and a reference region 78. Correspondingly, the sensor array 50 of FIG. 2 is divided into a region of testing sensors 56 and a region of reference sensors 58. One example arrangement of the testing sensors 56 and reference sensors 58 is shown in FIG. 2, however any suitable arrangement may be utilized. Assuming the tissue 72 is the same for the testing region 76 and the reference region 78, as well as piecewise homogenous, the testing region 76 may be equivalent to the reference region 78 excepting one heterogeneity, the STA 74. Bony support 82 is also shown in the tonometry model 70.

In one example, a step motor controlled dynamic compression procedure may be performed to determine elasticity of the tissue 72. The controlled compression, from contacting the tissue 72 to the maximized cardiac pulsation on the STA 74, is recorded by both the testing sensors 56 and the reference sensors 58, and therefore tissue elasticity can be calculated from a compression distance 80, as shown in FIG. 3.

Signals from the testing sensors 56 may be adaptively corrected by the signals from reference sensors 58 to enhance the contrast from the STA 74 and cancel interferences, such as sensor pressure drift. Both testing sensors 56 and reference sensors 58 output sensing data to a dual-sensor tonometry model. The elasticity of the STA 74 and the tissue 72 may also be measured and implemented in an algorithm to acquire absolute ABP measurements. The ABP measurement is performed at a location with near maximum cardiac pulsation, however, even if the cardiac pulsation changes, the reference sensors 58 detect the change, and the testing sensor 56 output is adjusted. This allows for an absolute ABP measurement to be made when the STA 74 has been compressed to a level which exhibits less than maximum cardiac pulsation.

Returning to FIG. 2, in one embodiment the sensor array 50 includes an 8×8 array of sensors 52 that are employed in a Parylene substrate 54. Thus, sixteen interconnects 60 are used to connect the 64 sensors 52. Based on a computational model that includes structural mechanics and electrostatics, the individual sensors 52 are expected to exhibit a sensitivity of about 0.2 fF/mmHg. Over the full 200 mmHg working range, the substrate 54 is expected to deflect by about 500 nanometers, approximately 25% of the compression distance 80, shown in FIG. 3. An electronic control unit 30, as shown in FIG. 1 and described in further detail below, can make use of a capacitance to digital conversion chip with capability to measure capacitance change with high resolution (~20 aF/Hz$^{1/2}$). Based on the predicted single sensor sensitivity (0.2 fF/mm Hg), the expected resolution of the system 10 is about 1 mm of Hg at a 100 sample per second update rate. An array of low-voltage complementary metal-oxide-semiconductor (CMOS) switches (not shown) may be used for routing the sensors 52 of FIG. 2 to be measured by one capacitance to digital conversion chip. Thus, the size and power of the system electronics is reduced and the number of interconnect lines 60 are more manageable. In other embodiments, the sensor array may consist of multiple piezoresistive or other type of pressure sensors.

In practice, when the sensor array 50 is applied to the tissue 72 near the STA 74, as shown in FIGS. 2 and 3, a portion of the sensors 52 may cover the STA 74 while the remaining sensors cover the surrounding tissue 72, due to the relatively large area of the sensor array 50. An algorithm automatically identifies and grounds the sensors 52 into testing sensors 56 and reference sensors 58.

Figure 4:
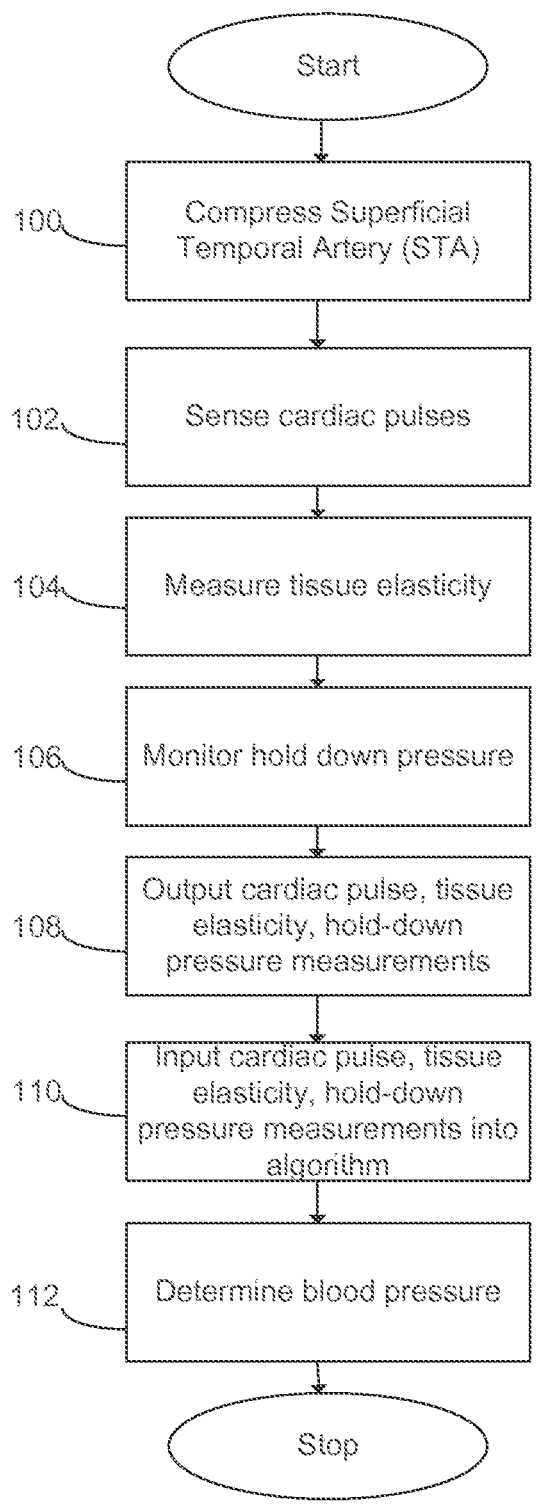
FIG. 4 is a flowchart illustrating a method for measuring blood pressure using STA tonometry.

Turning now to FIG. 4, is a flow chart illustrating a method for measuring blood pressure using STA tonometry is shown. To begin, the STA is compressed at process block 100. Next, the test sensor covers the STA location to pick up the major cardiac pulses at process block 102. While the reference sensor covers the adjacent tissue, defined as approximately 1 cm away from the STA location, the tissue elasticity may be measure at process block 104, and the hold-down pressure drift may be measured at process block 106. Next, at process block 108, the measurements of the associated cardiac pulse, tissue elasticity, and hold-down pressure drift are output by the sensors, and input into an algorithm at process block 110. The output of the algorithm determines the real-time blood pressure at process block 112.

Figure 5A:
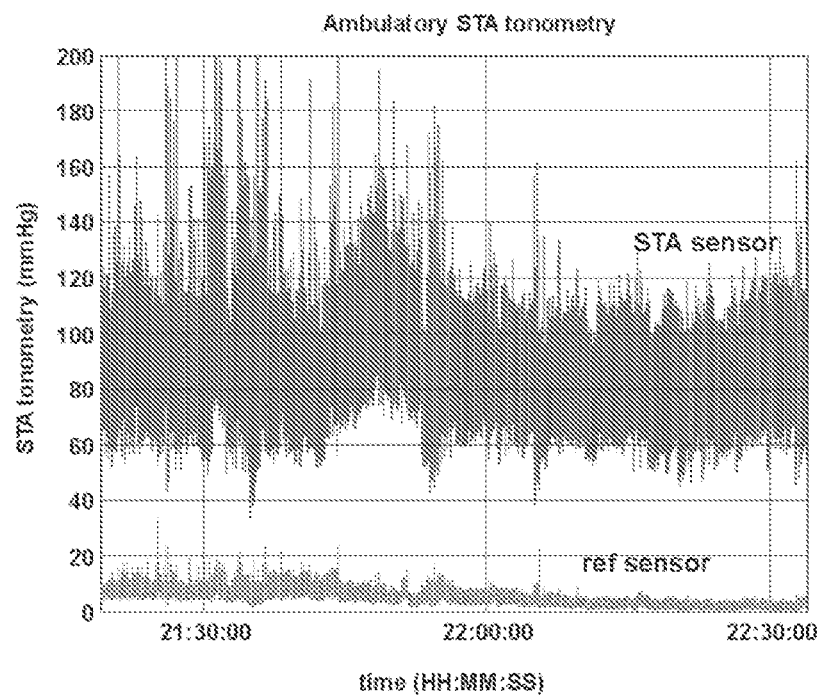
FIG. 5A is a graphical representation of dual-sensor STA tonometry results over time.

Turning now to FIG. 5A, an ambulatory monitoring result based on a single wrist blood pressure calibration is shown. In the example shown in FIG. 5A, the monitoring is relatively stable for over an hour. As a result, the reference sensor output demonstrates a similar decreasing drift trend to the STA test sensor, indicating a slight decrease in hold-down pressure. Thus, by applying adaptive signal correction using the reference sensor, the STA test sensor output can be further stabilized.

Figure 5B:
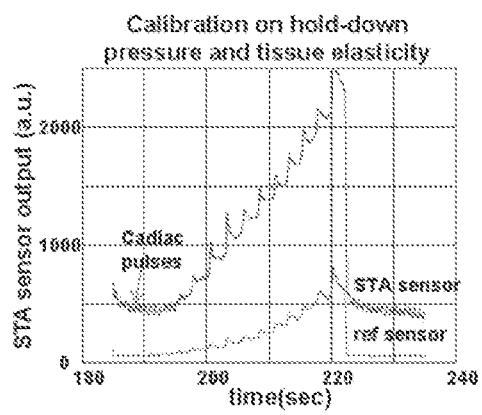
FIG. 5B is a graphical representation of a test sensor and reference sensor output as a response to dynamic increases in hold-down pressure.

FIG. 5B shows a dynamic hold-down pressure and tissue elasticity test result. Step-by-step increases in the hold-down pressure may be applied to the sensor pad 20, and an increase in both the test sensor 56 and reference sensor 58 output is shown with the increases in hold-down pressure. The tissue elasticity is also measured during the dynamic compression process. Both the test-reference sensor relationship and the tissue elasticity is recorded and used in the calibration and STA sensor drift correction. In some instances, at a certain hold-down pressure level, the cardiac pulses may disappear, which indicates occlusion of the STA, a feature used in auscultatory calibration.

Figure 5C:
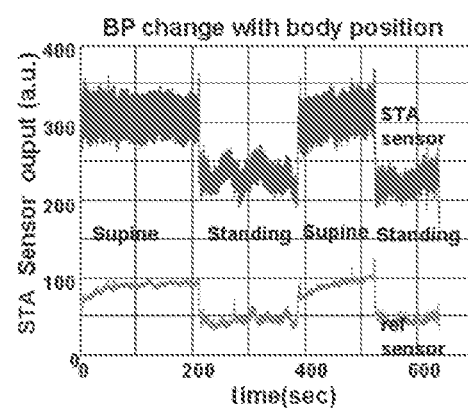
FIG. 5C is a graphical representation of ABP change over time as a response to a change in body position.

FIG. 5C shows the STA sensor and reference sensor outputs collected for hydrostatic calibration. It should be noted that both the DC component and the AC component increase in the supine position compared to the standing position. This repeatable signal change associated with body position change is used in the hydrostatic calibration of the STA tonometer 18.

In some embodiments, pulse transit time (PTT) and tissue hemodynamics, together with hydrostatics, are used to supplement the STA blood pressure measurement acquired with the blood pressure management system 10 of FIG. 1. To allow for acquisition of PTT, an electrocardiograph (ECG) reading may be used. When ECG is being sensed, at least one ECG sensor 26 is integrated within the frame 38 or the support 14 of the wearable device 12, as shown in FIG. 1, and ECG readings are separated from electroencephalograph (EEG) readings using wavelet and independent component analysis algorithms. The ECG sensors 26 are incorporated within the supports 14 to allow for ECG readings. The intervals between the QRS waves of the ECG waveform and the correspond optical heart pulsation peaks are calculated, and then converted into blood pressure using an algorithm.

When integrating the hydrostatic and tissue hemodynamics based approach, the head tissue of the user is illuminated using the hemodynamic sensors 22, which can be at least one of photodiodes and laser diodes. The head is illuminated using the hemodynamic sensors 22, for example at approximately 690 nanometers and 830 nanometers, followed by near infrared spectroscopy (NIRS) analysis to acquire tissue oxygenated hemoglobin and reduced hemoglobin concentrations. The tissue hemoglobin concentration changes are then combined with a hydrostatic pressure reference for absolute sensor calibration to acquire ABP.

The output of the three methods (i.e., STA tonometry, pulse transit time, and hydrostatic and tissue hemodynamics) just described are combined using a multi-modality algorithm to calculate an ABP measurement. It is also possible for the output of the three methods to be combined using individual signal quality indices (SQI). Each of the three methods may have interference sources which render the blood pressure measurement less reliable. Thus, the auxiliary sensors 24 may be incorporated within the frame 38 or the supports 14 to monitor the possible error sources, as shown in FIG. 1, and built-in to the SQI. SQI can also be calculated based on a signal's temporal, spectral, and statistical characteristics. SQIs are then combined using Kalman filter based techniques. In addition, drift, motion, and reposition interference identification and removal algorithms can be applied to the signals. This multi-modality approach can enhance the reliability and accuracy of ABP measurements acquired by the blood pressure management system 10.

When continuously recording the blood pressure during daily activities of the patient, it may be desirable to record while the patient is performing an activity that would have an effect on blood pressure. In a further embodiment, again referring to FIG. 1, one or more event buttons 28 may be attached to a lower edge the frame 38 or supports 14 of the wearable device 12 for easy access by the user. The event buttons 28 may be pressed by the user and record the when an activity has been performed.

Figure 6:
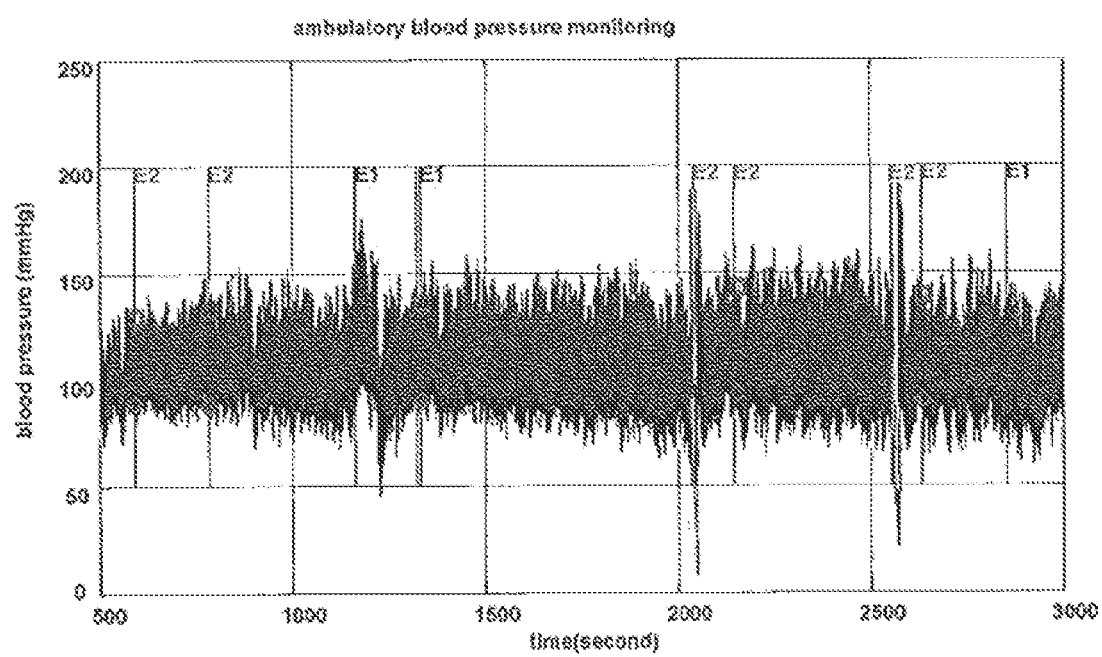
FIG. 6 is a graphical representation of measured blood pressure over time acquired using ambulatory STA blood pressure monitoring.

In one example, the blood pressure measurement system 10 may be utilized while the user perform regular activities including, but not limited to, working, walking, making phone calls, rest room breaks, and several Valsava maneuvers. During these activities, the blood pressure sensor 16 may be placed on the user's STA, and the user may be wearing the wrist blood pressure meter. External ECG, respiration, and motion sensors (not shown) may be placed on the chest and upper abdomen of the user. To obtain the associated physiological data, a long term ambulatory recorder can sample all channels at 250 Hz. Referring to FIG. 6, the ambulatory blood pressure monitoring result is shown. In this non-limiting example, the event buttons 28 corresponding to E1 and E2 were pressed during micturition and when the user performed a Valsava maneuver task, respectively.

As previously stated, the event button 28 corresponding to E1 in FIG. 6, was pressed during micturition in this example. In the ambulatory blood pressure recording, physiological blood pressure fluctuations were noted, and from the event marker and the diary log it is known that these blood pressure fluctuations are associated with maneuvers during micturition. The details of the related blood pressure recordings and the hemodynamics recordings are shown in FIGS. 7A and 7B.

From the tonometry result, an increase of systolic blood pressure in the magnitude of about 35 mmHg is shown in FIG. 7A, followed by a decrease of blood pressure in the magnitude of about −35 mmHg, and the total blood pressure swing reached 70 mmHg. Although different in magnitude, the diastolic blood pressure demonstrated the same swing pattern. This STA tonometry result was echoed by the independent hemodynamic recordings, where tissue oxygenated hemoglobin concentration increased about 8 μM during the ascending phase of blood pressure, and decreased about −8 μM during the descending phase. The tissue hemoglobin change demonstrated the same fluctuation pattern.

Figure 8A:
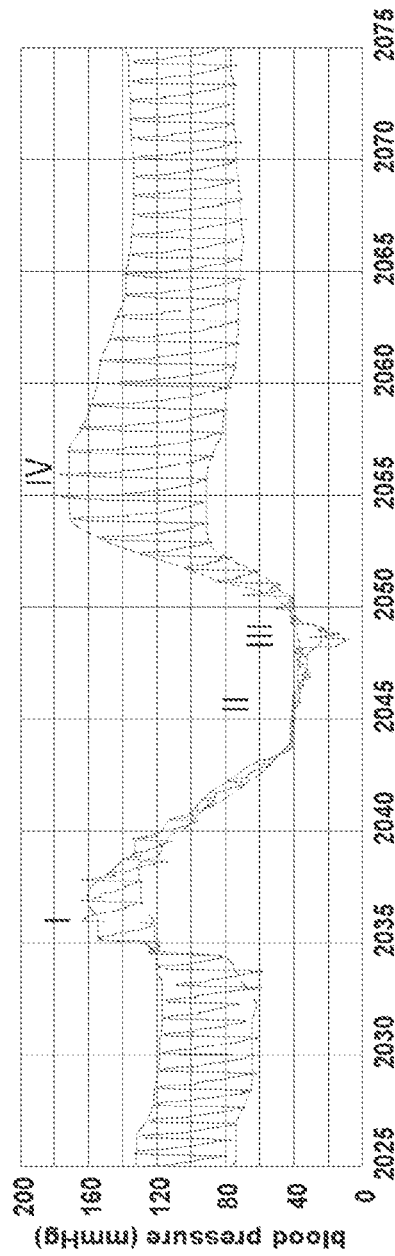
FIG. 8A is a graphical representation of measured blood pressure over time acquired using ambulatory STA tonometry during Valsalva maneuvers.
Figure 8B:
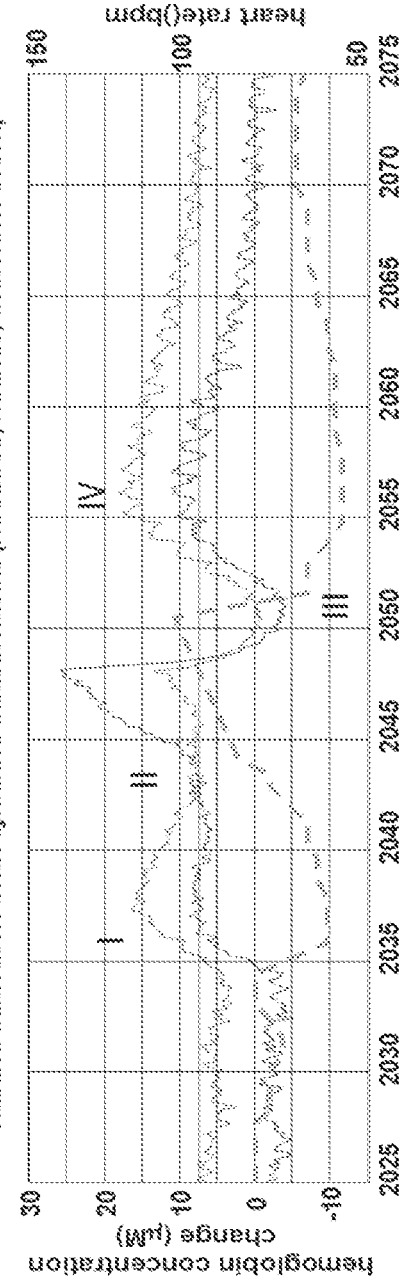
FIG. 8B is graphical representation of measured oxygenated hemoglobin and reduced hemoglobin concentrations acquired during Valsalva maneuvers.

The event button 28 corresponding to E2 in FIG. 6, may be pressed when the user conducts a Valsava maneuver, for example. As shown in FIG. 8, the four phases in the Valsava maneuver are shown. The phases include I) onset of straining with increased intrathoracic pressure, II) decreased venous return and consequent reduction of stroke volume and pulse pressure as straining continues, III) release of straining with decreased intrathoracic pressure and normalization of pulmonary blood flow, and IV) blood pressure overshoot with return of the heart rate to baseline. In phase I, a transient increase in the ABP, a strong increase in oxygenated hemoglobin concentration, and a small increase in reduced hemoglobin concentration are shown. In phase II, oxygenated hemoglobin concentration and reduced hemoglobin concentration decreased because of a fall in the ABP. With a release of strain, a sudden decrease in intrathoracic pressure was again transmitted to the arterial system and a transient decrease in the ABP occurred, resulting in the sudden decrease of oxygenated hemoglobin and reduced hemoglobin concentrations as shown in Phase III. Phase IV immediately followed with an overshoot in ABP, as well as oxygenated hemoglobin and reduced hemoglobin concentrations. This result again demonstrates the capabilities of a multi-modality recording system.

The above described simultaneous blood pressure and tissue hemodynamics monitoring result for a micturition maneuver may provide suggestions for the diagnosis of micturition syncope. The consistency between results from multiple modalities demonstrates the reliability of the recordings and also suggests the advantage of multi-modality blood pressure measurements.

In some embodiments of the blood pressure measurement system 10, it may be desirable to integrate the wireless electronic control unit 30 within one of the supports 14, as shown in FIG. 1. The electronic control unit 30 can be powered by the battery 32. In one example, the electronic control unit 30 may be incorporated into either support 14, however the electronic control unit 30 may be positioned in any suitable location of the wearable device 12. The wireless electronic control unit 30 may provide communication with an EHR system (not shown), for example. Additionally, or alternatively, the wireless electronic control unit 30 may provide communication with mobile devices, such as smart phones, and can integrate directly into online databases. Thus, short-term and real-time ambulatory blood pressure monitoring and data registration may be established. In addition, the wireless electronic control unit 30 may be used independently or together with a long-term ambulatory recording device.

Figure 9:
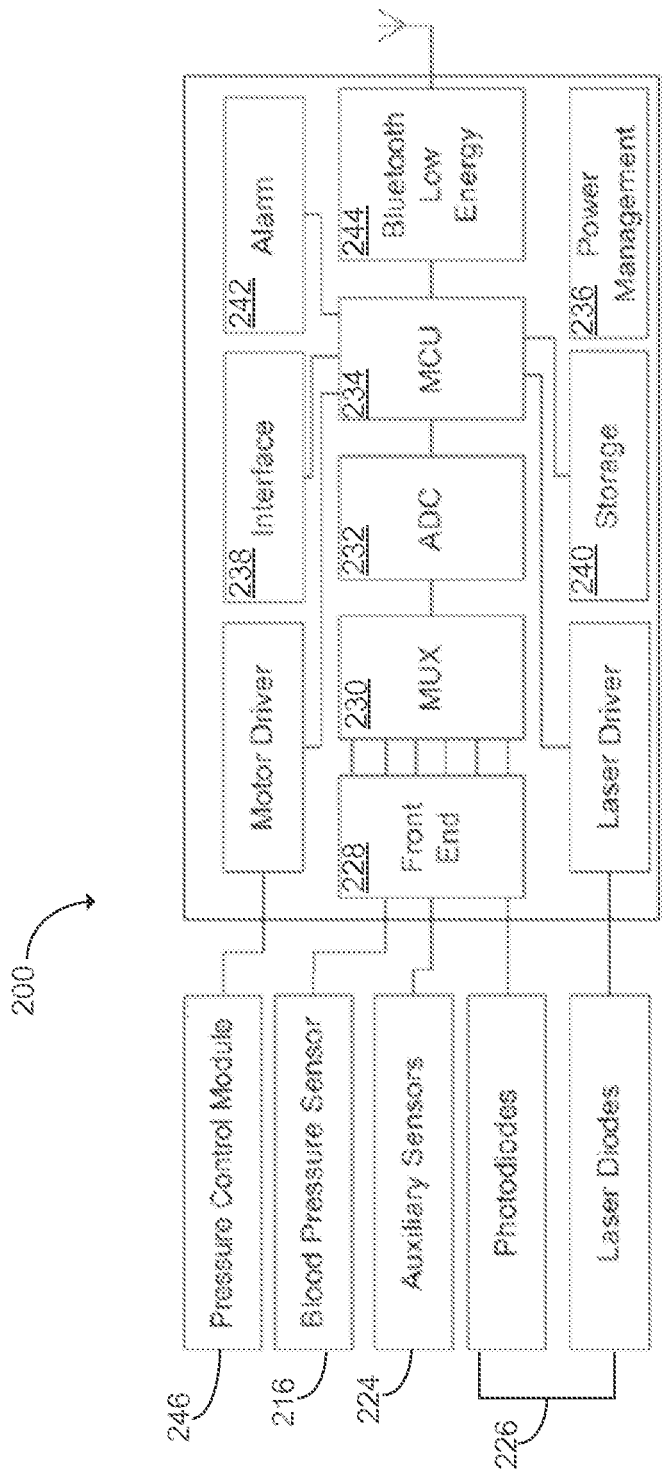
FIG. 9 is a schematic of example electronics embedded in the blood pressure management system of FIG. 1.

An example block diagram 200 of the electronic control unit 30 is shown in FIG. 9. As shown, a 16-channel integrated analog-front-end module 228 is provided for amplifying and filtering multiple-channel BP signals with high fidelity. A high-speed small-crosstalk multiplexer 230 is provided for routing 16-channel BP signals. A micropower 12-bit serial analog-to-digital converter (ADC) 232 is included to digitize signals at approximately 100 Hz. Additionally, a low-power microcontroller 234 may be embedded as a local processing unit for controlling the sensor array 50 and the ADC 232, handling a user interface 238, and running low-burden processing algorithms. A high-efficiency battery power management module 236 with short duty cycles is provided for the on-board components. The user interface 238 may be provided for user-machine interaction. The interface module 238 may include input-buttons to start/pause/stop data recording and to configure the recorder, for example. The interface module 238 may also have a screen to display recorder status. An on-the-board flash storage device 240 may also be included which has the capacity for ambulatory recording. A real-time alarm module 242 may be configured to alert the user and trigger data transmission to medical professionals, for example. A wireless module 244 allows data streaming to other devices, and an automatic tonometer pressure control 246 my be implemented to optimize the pressure of the pressure pad on the STA. In addition, blood pressure sensor 216, auxiliary sensors 224, and the photodiode and laser diode electrodes 226 for hemodynamic sensing can be implemented within the electronic control unit 30. A laser driver 248 can be provided to control the electrodes 226, and a motor driver 250 can be integrated to control the pressure control module 246.

In some embodiments, the blood pressure measurement system 10 may be integrated with an electronic health record (EHR) system for synchronization with other signals, data archiving, analysis, query and both real-time and historical display. In the embodiments provided with wireless connection capabilities, a "listener" code module for the EHR platform may sense the blood pressure measurement system 10 as it is turned on, automatically collect and store the data that is generated, and enable data query and visual display of these recordings. Individual measurement devices can be marked with different model numbers, to enable separation of signals from each individual.

The EHR's automatic data archiving enables tracking of blood pressure over extended periods of time with limited action required by the user. The system is robust to internet or other connectivity outages, seamlessly switching between store-and-forward versus real-time communication as required, and makes the data available for query through a web service, such as a browser.

In another non-limiting example, the blood pressure management system 10 can connect with Bluetooth devices, such as Bluetooth low energy (BLE) devices via a Generic Attribute Profile (GATT). An application can be used on a mobile device, for example, running in either high-performance or energy-saving mode. This application can con be configured to acquire data from a recorder via Bluetooth, process the data, and create a data visualization on the GUI. When WiFi/3G/4G connections are available, the data can be synchronized to send blood pressure data to a central server in a doctor's office or a hospital.

Figure 10:
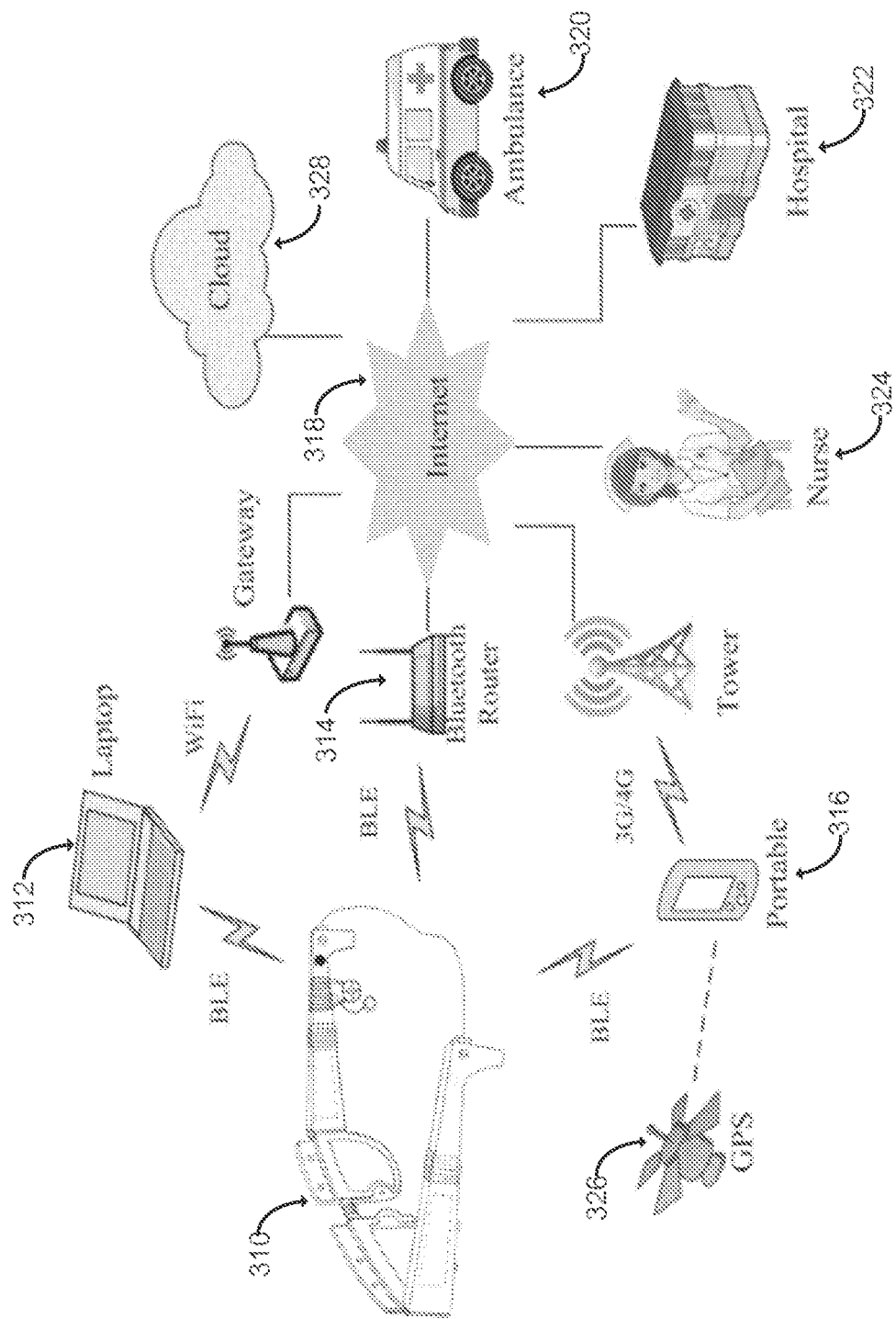
FIG. 10 is a schematic of the connection capabilities of an embodiment of the blood pressure management system.

Additional connection capabilities are shown in FIG. 10. The blood pressure management system 310 may connect via BLE to a laptop 312, a Bluetooth router 314, or a mobile device 316. The mobile device 316 can be in communication with a global positioning system (GPS) 326, allowing for data collection regarding the location of the user. The Bluetooth router 314 may provide connection between the blood pressure management system 310 and an internet service 318. The internet service 318 can additionally allow for data from the blood pressure management system 310 to be transmitted to a remote server 328 for centralized data storage, an ambulance or other medical transportation 320, a medical facility 322, or medical personnel 324.

The present invention has been described in terms of one or more preferred embodiments, and it should be appreciated that many equivalents, alternatives, variations, and modifications, aside from those expressly stated, are possible and within the scope of the invention.

What is claimed is:

1. A blood pressure measurement and monitoring device, the device comprising:
   a wearable device;
   a tonometry device coupled to the wearable device and configured to compress a superficial temporal artery (STA);
   a sensor pad attached to the wearable device and adjacent the tonometry device;
   a sensor array integrated within the sensor pad for continuous, unobtrusive blood pressure monitoring, the sensor array having a first pressure sensor that is a testing sensor, and a second pressure sensor that is a reference sensor;
   an electric control unit in communication with the sensor array, the electric control unit configured to:
      receive first pressure data from the testing sensor;
      receive second pressure data from the reference sensor;
      correct the first pressure data using the second pressure data to generate a corrected pressure signal;
      determine, using the corrected pressure signal, an arterial blood pressure measurement; and
      generate a real-time alert based on the arterial blood pressure measurement,
   wherein a tissue of the subject includes a testing region and a reference region, the testing region including the STA, and the reference region not including the STA, and
   wherein when the sensor array is positioned on the subject, a surface of the testing sensor is configured to contact the testing region and a surface of the reference sensor is configured to contact the reference region.

2. The device of claim 1 wherein the wearable device includes at least one of a hat, a headband, and headphones.

3. The device of claim 1 wherein the wearable device includes a pair of glasses having a frame and a pair of temples, and
wherein at least one of a width of the frame and a length of temples are adjustable.

4. The device of claim 1, wherein the sensor array includes a plurality of pressure sensors that are configured in a two-dimensional array,
wherein the two-dimensional array of sensors comprises a plurality of rows of pressure sensors and a plurality of columns of pressure sensors, and
wherein the plurality of pressure sensors includes the first pressure sensor and the second pressure sensor.

5. The device of claim 4, wherein the two-dimensional sensor array includes a row of interconnects and a column of interconnects, and the device further comprises a switching device, the switching device being configured to:
activate a first interconnect within the row of interconnects;
activate a second interconnect within the column of interconnects; and
receive pressure data from the pressure sensor within the two-dimensional sensor array that interfaces with the activated first interconnect and the activated second interconnect.

6. The device of claim 1, wherein the arterial blood pressure measurement is a first arterial blood pressure measurement, the device further comprising:
a hemodynamic sensor coupled to the wearable device, the hemodynamic sensor configured to emit light, and sense optical data based on the emitted light; and
an ECG sensor coupled to the wearable device and configured to sense ECG data; and
wherein the electric control unit is further configured to:
cause the hemodynamic sensor to emit light;
receive optical data from the hemodynamic sensor, based on the emitted light;
receive ECG data from the ECG sensor;
determine a second arterial blood pressure measurement based on the optical data and the ECG data.

7. The device of claim 1 further comprising pulse wave velocity (PWV) sensors, the PWV sensors configured to measure at least one of a time and a speed of a cardiac pulse propagation along the STA.

8. The device of claim 1, wherein the electric control unit is coupled to the wearable device, and
wherein the electric control unit is configured to provide wireless communication to an electronic health record system.

9. The device of claim 1, wherein the first pressure data is acquired when the subject is in a standing position, and the electric control unit is further configured to
receive third pressure data from the testing sensor when the subject is in a supine position; and
calibrate the sensor array, based on the first pressure data and the third pressure data.

10. The device of claim 1, wherein the electric control unit is further configured to:
determine the testing sensor within the sensor array, and
determine the reference sensor within the sensor array.

11. The device of claim 1, wherein the sensor array includes a flexible substrate, the flexible substrate being configured to conform to nonplanar geometries when the sensor array is positioned on the subject.

12. The device of claim 1, wherein the sensor pad is configured to adjust a pressing angle of the sensor array, and further comprising at least one of a spring and a screw coupled to the sensor pad, the at least one of the spring and the screw configured to apply an external pressure to the STA.

13. The device of claim 1, wherein the electric control unit is further configured to:
determine a compression distance of the sensor array from the tonometry device compressing the STA, the compression distance being defined as an axial distance the tonometer travels starting when the tonometry device contacts tissue of the subject; and
determine an elasticity of the tissue surrounding the STA based on the compression distance.

14. The device of claim 13, wherein the electric control unit is further configured to determine the arterial blood pressure measurement based on the first pressure data, the second pressure data; and the elasticity of the tissue surrounding the STA.

15. The device of claim 1, wherein the electric control unit is further configured to:
determine a correction from the second pressure data from the reference sensor; and
apply the correction to the first pressure data from the testing sensor to determine the arterial blood pressure measurement.

16. A method for monitoring blood pressure of a subject, the method comprising:
compressing a superficial temporal artery (STA) using a tonometer;
contacting tissue that includes the STA using a sensor array;
receiving, from the sensor array, a pressure measurement for the STA;
determining a compression distance from the compressing of the STA, the compression distance being defined as an axial distance the tonometer travels starting when the tonometer contacts tissue of the subject;
determining an elasticity of a tissue surrounding the STA based on the compression distance;
determining a blood pressure measurement based on the elasticity of the tissue surrounding the STA and the pressure measurement; and
generating a real-time alert based on the blood pressure measurement.

17. The method of claim 16 wherein the sensor array includes a testing sensor and a reference sensor, the testing sensor being a pressure sensor, and the reference sensor being a second pressure sensor, when the sensor array contacts the tissue, the testing sensor is adjacent to the STA and the reference sensor is situated away from the STA, such that a surface of the reference sensor contacts tissue not including the STA; and
wherein receiving the pressure measurement comprises receiving cardiac pulses of the STA from the testing sensor; and
wherein the method further comprises receiving pressure data from the reference sensor.

18. The method of claim 17 further comprising:
comparing the cardiac pulses with the pressure data from the reference sensor;
determining a hold-down pressure drift from the comparison between the cardiac pulses and the pressure data from the reference sensor; and calibrating the sensor array based on the hold-down pressure drift.

19. The method of claim 17 further comprising:
recording an electrocardiograph (ECG) waveform with an ECG sensor;
determining a pulse transit time from the ECG waveform;
measuring a hemodynamic signal with a hemodynamic sensor, the hemodynamic sensor being configured to emit light, and receive optical data based on the emitted light,
wherein the blood pressure measurement is further based on the ECG waveform and the optical data.

20. The method of claim 19, wherein the cardiac pulses are sensed when the subject is in a standing position, and further comprising:
acquiring second pressure data from the testing sensor when the subject is in a supine position;
determining a hydrostatic calibration based on the cardiac pulses and the second pressure data;
determining a refined arterial blood pressure based on the cardiac pulses from the testing sensor, the arterial blood pressure, and the hydrostatic calibration.

21. The method of claim 17, further comprising calibrating the sensor array, based on the cardiac pulses, and the pressure data.

22. The method of claim 17, further comprising actuating an event button,
wherein the cardiac pulses are sensed and the pressure data is received after actuation of the event button; and
wherein the even button is actuated prior to a subject performing at least one of a Valsalva maneuver, and a micturition event.

23. A blood pressure measurement device comprising:
a wearable device;
a tonometry device coupled to the wearable device and configured to compress a superficial temporal artery (STA) when the tonometry device is positioned on a tissue of a subject including the STA;
a sensor pad attached to the wearable device and adjacent the tonometry device;
a sensor array integrated within the sensor pad for continuous, unobtrusive blood pressure monitoring, the sensor array having a first pressure sensor that is a testing sensor, and a second pressure sensor that is a reference sensor; and
an electric control unit in communication with the sensor array and the tonometry device, the electric control unit configured to:
determine a compression distance from the compressing of the STA, the compression distance being defined as an axial distance the tonometry device travels starting when the tonometry device contacts tissue of the subject;
determine an elasticity of a tissue surrounding the STA based on the compression distance;
determine, from the sensor array, a blood pressure signal;
determine an arterial blood pressure measurement, based on the blood pressure signal and the elasticity of the tissue; and
generate a real-time alert based on the arterial blood pressure measurement,
wherein when the sensor array is positioned on a tissue of the subject, the testing sensor is configured to contact a testing region of the tissue, and the reference sensor is configured to contact a reference region of the tissue, the testing region not including the STA, and the reference region not including the STA.

24. The device of claim 23, wherein the blood pressure signal is a corrected pressure signal; and
wherein the electric control unit is further configured to:
receive, from the testing sensor, a first pressure signal;
receive, from the reference sensor, a second pressure signal; and
correct the first pressure signal using the second pressure signal to generate the corrected pressure signal.

25. The device of claim 24, wherein the electric control unit is further configured to:
determine, using the second pressure signal, a hold-down pressure drift; and
correct the first pressure signal using the determined hold-down pressure drift to generate the corrected pressure signal.

26. The device of claim 24, wherein the electric control unit is further configured to
correct the first pressure signal using the elasticity of the tissue to generate the corrected pressure signal.

27. The device of claim 24, wherein a distance between the reference sensor and the testing sensor is at least 1 centimeter.

* * * * *